United States Patent
Sharma et al.

(10) Patent No.: US 7,659,244 B2
(45) Date of Patent: Feb. 9, 2010

(54) RAPAMYCIN PEPTIDES CONJUGATES: SYNTHESIS AND USES THEREOF

(75) Inventors: Sanjay K. Sharma, Edmonton (CA); Thomas Woo, Edmonton (CA); Selvaraj Naicker, Edmonton (CA)

(73) Assignee: Quest Pharmatech, Inc., Edmondton, Alberta (CA)

( * ) Notice: Subject to any disclaimer, the term of this patent is extended or adjusted under 35 U.S.C. 154(b) by 570 days.

(21) Appl. No.: 10/578,105

(22) PCT Filed: Nov. 3, 2004

(86) PCT No.: PCT/CA2004/001918

§ 371 (c)(1),
(2), (4) Date: Jan. 10, 2007

(87) PCT Pub. No.: WO2005/042567

PCT Pub. Date: May 12, 2005

(65) Prior Publication Data

US 2007/0129394 A1    Jun. 7, 2007

(51) Int. Cl.
*A61K 38/12* (2006.01)
*C07K 7/50* (2006.01)
(52) U.S. Cl. .......................... 514/9; 530/317
(58) Field of Classification Search ............ None
See application file for complete search history.

(56) References Cited

U.S. PATENT DOCUMENTS

| 5,385,910 A | 1/1995 | Ocain et al. |
| 5,411,967 A | 5/1995 | Kao et al. |
| 6,585,764 B2 | 7/2003 | Wright et al. |

FOREIGN PATENT DOCUMENTS

| EP | 0509795 A3 | 10/1992 |
| WO | WO 96/41807 | 12/1996 |
| WO | WO 03/057218 A1 | 7/2003 |

OTHER PUBLICATIONS

International Search Report and Written Opinion of the International Searching Authority, corresponding to PCT application No. PCT/CA2004/001918 dated Mar. 14, 2005.

*Primary Examiner*—Andrew D Kosar
(74) *Attorney, Agent, or Firm*—Jenkins, Wilson, Taylor & Hunt, P.A.

(57) ABSTRACT

The present invention relates to new rapamycin derivatives for the inhibition of cell proliferation. The compounds can advantageously target two proteins in dividing cells and interfere with cell cycle. There is thus provided derivatives of rapamycin in which the 42 position of rapamycin is linked to an amino acid or a peptide through a carbamate ester linkage. These rapamycin derivatives can be synthesized by reacting 42-O-(4-Nitrophenoxycarbonyl) rapamycin and an amino acid or a free amino peptide under basic conditions. These rapamycin derivatives can be used to inhibit the cell cycle and are therefore useful for treating cell proliferation disorders.

20 Claims, No Drawings

RAPAMYCIN PEPTIDES CONJUGATES: SYNTHESIS AND USES THEREOF

TECHNICAL FIELD

This application relates to cell cycle inhibitors. More particularly the invention relates to the synthesis of rapamycin peptides conjugates and their use in treating disorders related to cell division.

BACKGROUND OF THE INVENTION

Cancer drug discovery is one of the most rapidly changing areas of pharmaceutical research. Most anticancer agents that are approved for clinical use are molecules which damage deoxyribonucleic acid (DNA), block DNA synthesis indirectly through inhibition of nucleic acid precursor biosynthesis or disrupt hormonal stimulation of cell growth (Sielecki, T. M. et al. *J. Med. Chem.* 2000, 43 (1), 1-18). There has been a recent shift of emphasis towards novel mechanistic targets that has emerged as a direct consequence of the intense study of the underlying genetic changes associated with the cancerous state. The high frequency of mutations in cancer cells which results in altered cell cycle regulation, in conjunction with aberrant expression of cyclin dependent kinases (CDKs) and growth signal transduction, conferring a proliferative advantage, indicates that many of these aberrant mechanisms may be strategic targets for cancer therapy. An increasing body of evidence has shown a link between tumor development and CDK related malfunctions. Over expression of the cyclic regulatory protein and subsequent kinase hyperactivity have been linked to several types of cancers. The process of cell division has been amply studied but the molecular mechanisms that regulate the cell cycle have only been elucidate in the last two decades. The phases of the cell cycle are: The rest phase, $G_o$, active protein synthesis in preparation of cell division occurs in the $G_1$ phase. During the $G_1$ phase the volume of the cell increases. After the $G_1$ phase the cells enter the S phase in which the DNA is replicated. The S phase is followed by another gap phase, $G_2$, during which DNA replication is completed. The last phase is the mitosis or M phase in which the cells divide (Muhtasib, H. G. et al. *Curr. Cancer Drug Targets* 2002, 2, 309-336).

Rapamycin (Sirolimus, Rapamune, 1,18-dihydroxy-12-[2 (4-hydroxy-3-methoxy-cyclohexyl)-1-methyl-ethyl]-19,30-4-aza-tricyclo[30.3.1% 4,9 &]hexatriaconta-16,24,26,28-tetraene-2,3,10,14,20-pentaone) with a molecular formula of $C_{51}H_{79}NO_{13}$ and molecular mass of 913.6 Da was isolated in 1975 from the bacteria strain *Streptomyces hygroscopicus* found in a soil sample on Ester Island (Sehgal, S. N. et al. *J. Antibiot.* 1975, 28, 721 and Sehgal, S. N. et al. *J. Antibiot.* 1975, 28, 727). Rapamycin has potent antimicrobial, immunosuppressant and antitumor properties. It inhibits the translation of key mRNAs of proteins required for the cell cycle progression from $G_1$ to S phase by binding intracellularly to the immunophilin FK506 binding protein FKBP12 and the resultant complex inhibits the protein kinase activity of a protein kinase termed mammalian target of rapamycin (mTOR). The inhibition of mTOR, in turn blocks signals to two separate downstream pathways which control the translation of specific mRNA (40S ribosomal protein S6 kinase $p70^{S6K}$) required for cell cycle traverse from $G_1$ to S phase (Wiederrecht, G. J. et al. *Prog. Cell. Cycle. Res.* 1995, 1, 53-71).

The poor aqueous solubility and chemical stability of rapamycin precluded its clinical development as an anticancer agent. Recently a series of rapamycin analogs with improved aqueous solubility and stability have been synthesized and evaluated. CCI-779 (Wyeth Ayerst, Pa., USA), a soluble ester analog of rapamycin is selected for development as an anti cancer agent based on its prominent antitumor profile and favourable pharmaceutical and toxicological characterstics in preclinical studies (Huang,. S. et al. *Curr. Opin. Investig. Drugs* 2002, 3, 295-304). CCI-779 has demonstrated significant inhibitory effects both in vivo and in vitro (various cell lines lines with $IC_{50}$ values of $<10^{-8}$ M). Its cytostatic properties results from the inhibition of translation of several key proteins that regulate the $G_1$ phase of the cell cycle. Similar to rapamycin, CCI-779 is hypothesized to form a complex with the intracellular cytoplasmic protein FK506 binding protein $-12$ (FKBP) that binds to mTOR resulting in the inhibition of key signaling pathways involved in the $G_1$ phase of the cell cycle and thereby checks the progression from $G_1$ to S phase. Studies have shown that CCI-779 is able to penetrate the blood brain barrier as it has aqueous solubility and is highly lipophilic. Phase I and II studies have shown that CCI-779 is associated predominantly with skin toxicities (rash, folliculitis, prurtis, ulceration and nail changes), stomatic and asthenia (Elit, L. *Curr Opin. Investig. Drugs* 2002, 3, 1249-1253 and Punt, C. J. A. et al. *Annals of Oncology* 2003, 14, 931-937).

The CDK complex activity. is regulated by mechanisms such as stimulatory or inhibitory phosphorylations as well as the synthesis and degradation of the kinase and cyclin subunits themselves. Recently a link has been established between the regulation of the activity of the cyclin dependent kinases and cancer by the discovery of a group of CDK inhibitors including $p27^{Kip1}$, $p21^{Waf1/Cip1}$ and $p16^{Ink4/MTS1}$. The inhibitory activity of $p27^{Kip1}$ is induced by the negative growth factor TGF-β and by contact inhibition (Nurse et al. *Nature* 1994, 372 (8), 570-573). The interleukin-2 (IL-2) allows CDK activation by causing the elimination of the CDK inhibitor protein $p27^{Kip1}$, which effect is prevented by rapamycin. By contrast, the CDK inhibitor p21 is induced by IL-2 and this induction is blocked by rapamycin. The activity of $p21^{Waf1/Cip1}$ is regulated transcriptionally by DNA damage through the induction of p53, senesence and quiesence. The tumor suppressor protein $p21^{Waf1}$ plays a central role in regulating eukaryotic cell-cycle progression. Through its association with $G_1$ and S phase CDK complexes it regulates activation of the retinoblastoma protein (pRb) and E2F transcription factors. Thus, selective blockade of the cyclin recruitment site would prevent recognition and subsequent phosphorylation of CDK substrates, and therefore offers a therapeutic approach towards restoration of $p21^{Waf1}$ like tumor suppression. Recently the octapeptide, HSKRRLIF, located C-terminal in $p21^{Waf1}$ which has been shown to display potent cyclic inhibitory activity due to its capacity to bind to the cyclic recruitment site. These proteins $p27^{Kip1}$, $p21^{Waf1/Cip1}$ and $p16^{Ink4/MTS1}$, when bound to CDK complexes, inhibit their kinase activity, thereby inhibiting progression through the cell cycle (Chen, Y. P. et al. *Proc. Natl. Acad. Sci. USA* 1999, 96, 4325-29; Zheleva, D. I. et al. *J. Peptide Res.* 2002, 60, 257-270; Atkinson, G. E. et al. *Bioorg. Med. Chem. Lett.* 2002, 12, 2501-2505; McInnes, C. et al. *Curr. Med. Chem. -Anticancer Agents* 2003, 3, 57-69.

There is therefore a need for compounds that can target the function of cell cycle suppressors such as p27$^{Kip1}$ and p21$^{Waf1/Cip1}$.

SUMMARY OF THE INVENTION

The present invention relates to new rapamycin derivatives for the inhibition of cell proliferation. The compounds advantageously combine two molecular functionalities that can target the functions of two or more proteins in dividing cells and interfere with cell cycle.

In one embodiment of the invention there is provided derivatives of rapamycin in which the 42 position of rapamycin is linked to an amino acid, or an amino alcohol, or a peptide through a carbamate ester linkage. These rapamycin derivatives can be synthesized by reacting 42-O-(4-Nitrophenoxycarbonyl)rapamycin and an amino acid, or amino alcohol, or an amino peptide under basic conditions.

In a further embodiment the rapamycin derivatives can be used to inhibit the cell cycle and are therefore useful for treating cell proliferation disorders selected from cancer, hyperplasia, psoriasis and hyperproliferative vascular disease.

The compounds or compositions of the present invention can be released from a carrier, and the carrier can be implanted at a desired location within a patient using for example a cathether.

In a further embodiment there is provided a stent coated with the compound of the present invention for the treatment of a hyperproliferative vascular disease.

In yet a further embodiment pharmaceutical compositions comprising a compound of the invention or a pharmaceutically acceptable salt thereof, and a pharmaceutically acceptable carrier can be used as an immunosuppressant for treating an immunological condition such as autoimmune disease and host-graft disease.

Further features and advantages of the present invention will become apparent from the following detailed description.

DETAILED DESCRIPTION OF THE PREFERRED EMBODIMENT

This invention relates to the synthesis of novel rapamycin derivatives compounds useful for the inhibition of cell division for the treatment of diseases in which the inhibition of cell proliferation is desirable having the structure

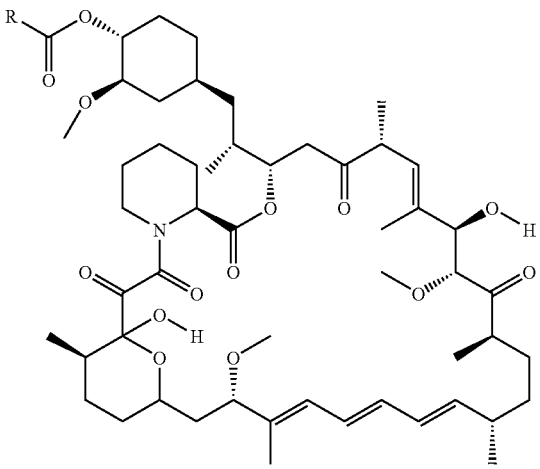

wherein,
R is NH-(A)$_n$-CH$_2$OH;

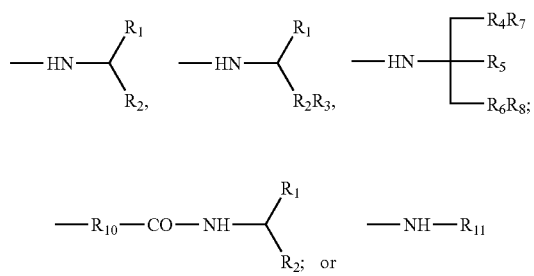

A is D or L amino acid, and n=1-10, A is preferably combinations of amino acids as shown in compounds 7a-7i, R$_1$ and R$_2$ are each independently, hydrogen, alkyl of 1-6 carbons atoms, hydroxyalkyl of 1-6 carbon atoms, or CO$_2$R$_9$, R$_3$ is Ar, wherein Ar is aromatic or hetroaromatic, R$_4$, R$_5$ and R$_6$ are each independently alkyl of 1-6 carbon atoms or hydroxyalkyl of 1-6 carbon atoms, R$_7$ and R$_8$ are each independently hydrogen, cycloalkyl of 1-6 carbon atoms or hydroxycycloalkyl of 3-16 carbon atoms, and R$_9$ is alkyl of 1-6 carbon atoms, R$_{10}$ is alkyl of 1-10 carbon atoms and R$_{11}$ is cycloalkoxyalkyl of 3-10 carbon atoms.

In one embodiment, amino acids and/or small peptides derivatives of the octapeptide HSKRRLIF are conjugated with rapamycin (formula 5). The regioselective synthesis of derivatives of rapamycin 5 at the 42 position, is achieved by conjugating the amino end of the amino acids and/or active peptides with 42-O-(4-Nitrophenoxycarbonyl) rapamycin (6). Compounds of general formula 7 (Scheme 1) are thereby obtained.

Scheme 1
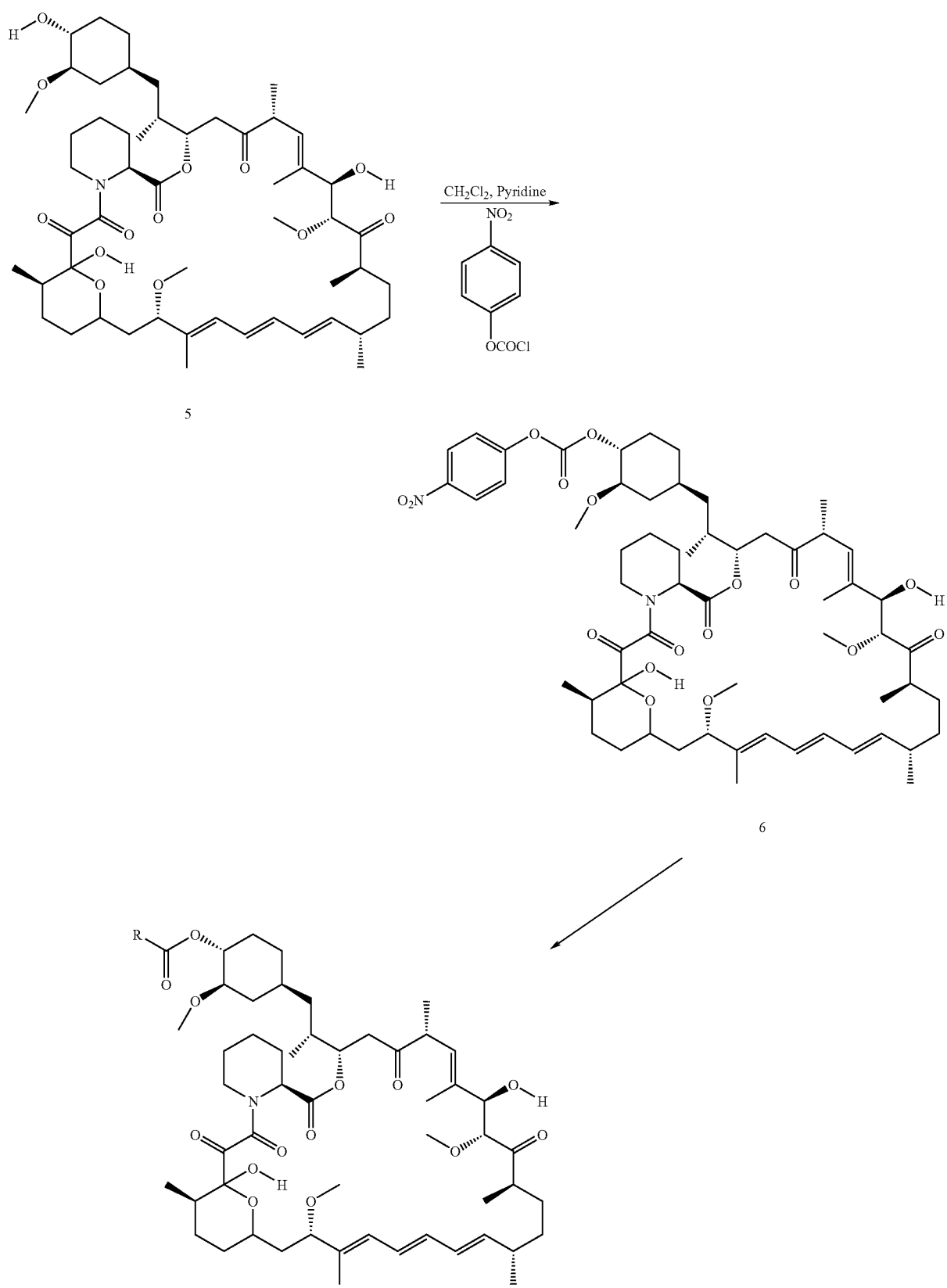

The peptides conjugated to rapamycin preferably comprise amino acids from the C-terminal of the octapeptide HSKRR-LIF. The amino acids at the N-terminal may differ from that of the octapeptide. Single amino acids may also be used. Examples of compounds obtained by the combination of 42-O-(4-Nitrophenoxycarbonyl) rapamycin and amino acids and/or peptides are given below (compounds 7a to 7v).

The peptides used to derive 42-O-(4-Nitrophenoxycarbonyl) rapamycin can be synthesized from amino alcohols. The first amino acid is kept as Phe—OH (or 2-amino-3-phenyl-propanol) and performing chain elongation with Fmoc chemistry in solution phase (Scheme 2) using DCC/HOBt as the coupling reagents.

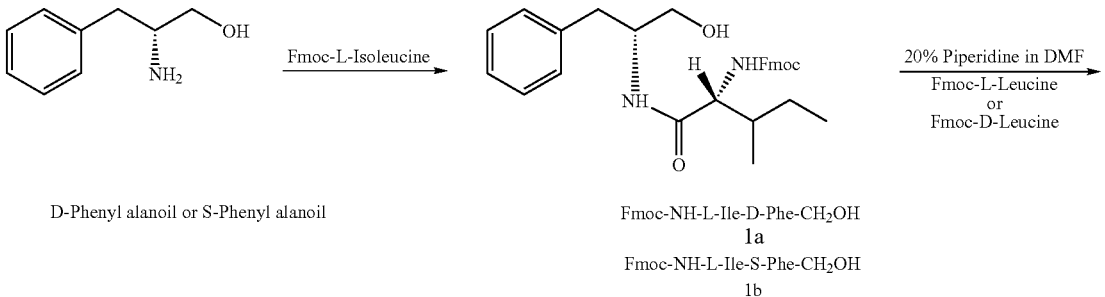

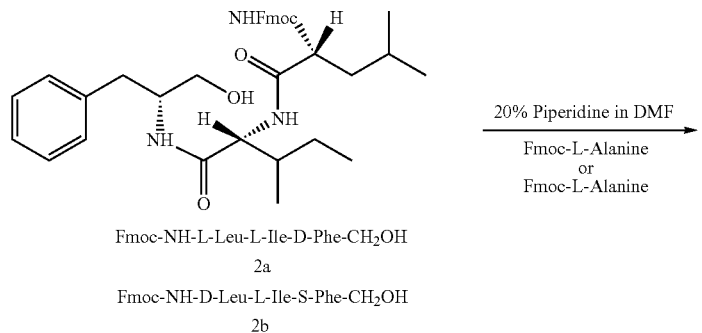

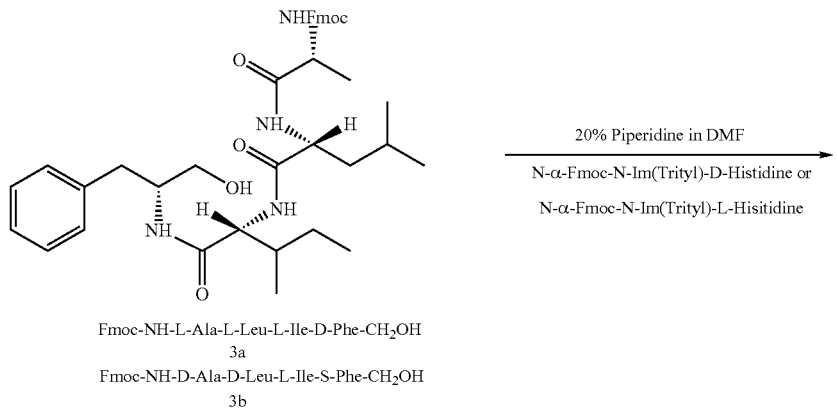

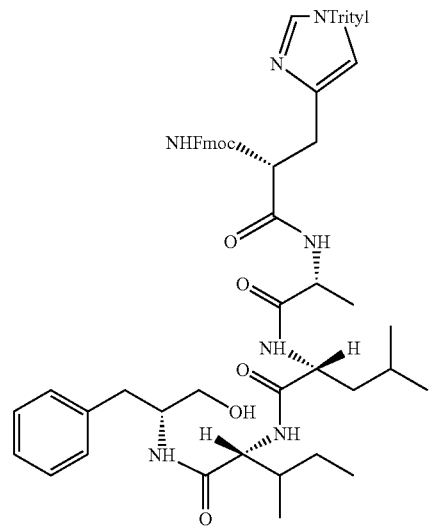

N-α-Fmoc-N-Im(Trityl)-D-His-
L-Ala-L-Leu-L-Ile-D-Phe-CH$_2$OH

4a

N-α–Fmoc-N-Im(Trityl)-L-His-L-
Ala-L-Leu-L-Ile-D-Phe-CH$_2$OH

4b

The subsequent coupling of the peptide sequence with 42-O-(4-Nitrophenoxycarbonyl) rapamycin is done first by de-blocking the Fmoc group under basic conditions (using piperidine for example) and then by coupling the peptide with 42-O-(4-nitrophenoxycarbonyl) rapamycin (6) under basic conditions as shown in scheme 3 to obtain compounds of general formula 7.

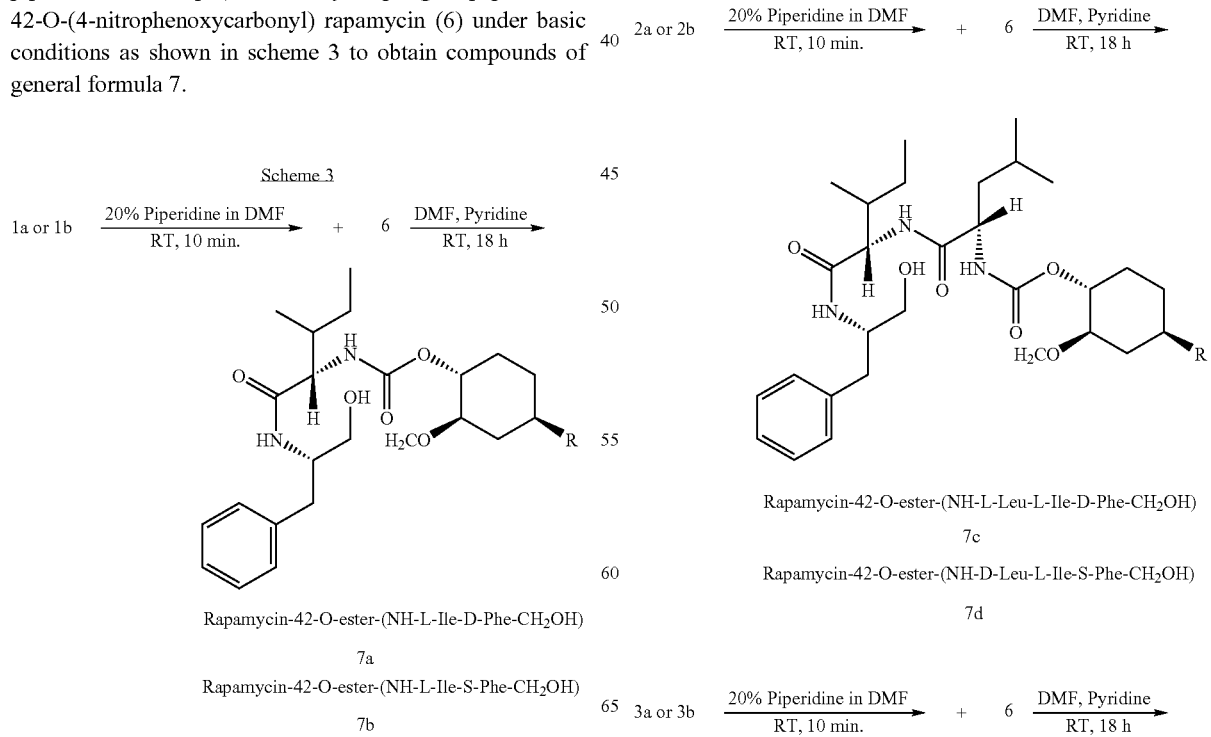

Rapamycin-42-O-ester-(NH-L-Ala-L-Leu-L-Ile-D-Phe-CH₂OH

7e

Rapamycin-42-O-ester-(NH-D-Ala-D-Leu-L-Ile-S-Phe-CH₂OH

7f 4a or 4b $\xrightarrow{\text{20\% Piperidine in DMF}}_{\text{RT, 10 min.}}$ + 6 $\xrightarrow{\text{DMF, Pyridine}}_{\text{RT, 18 h}}$ $\xrightarrow{\text{1\% Acetic acid, 1 h}}$ Rapamycin-42-O-ester-(NH-Im(Trityl)-D-His-L-Ala-L-Leu-L-Ile-D-Phe-CH₂OH)

7g

Rapamycin-42-O-ester-(NH-Im(Trityl)-L-His-L-Ala-L-Leu-L-Ile-D-Phe-CH₂OH)

7h

The derivatives of rapamycin at the 42 position may also be synthesized by conjugating the amino end of amino alcohols. Compounds 7j to 7v are examples of such amino alcohols-rapamycin conjugates (Sheet 1).

Sheet 1

7

NH-L-Ile-D-Phe-CH₂OH

7a

NH-L-Ile-S-Phe-CH₂OH

7b

NH-L-Leu-L-Ile-D-Phe-CH₂OH

7c

NH-D-Leu-L-Ile-S-Phe-CH₂OH

7d

NH-L-Ala-L-Leu-L-Ile-D-Phe-CH₂OH

7e

NH-D-Ala-D-Leu-L-Ile-S-Phe-CH₂OH

7f

NH-N-Im(Trityl)D-His-L-Ala-L-Leu-L-Ile-D-Phe-CH₂OH

7g

NH-N-Im(Trityl)D-His-L-Ala-L-Leu-L-Ile-D-Phe-CH₂OH

7h

NH-L-His-L-Ala-L-Lys-L-Arg-L-Arg-L-Leu-L-Ile-D-Phe-CH₂OH

7i

R = HO—CH₂—CH—CH₂C₆H₅ (with HN— substituent)

7j

R = HO—CH₂—CH—CH₂C₆H₅ (with HN— substituent)

7k

R = HO—CH₂—CH—CHC₆H₅ (with HN— substituent and OH)

7l

-continued

R = 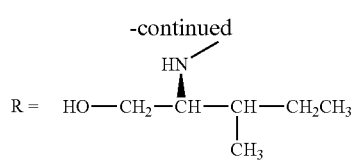
7m

R = 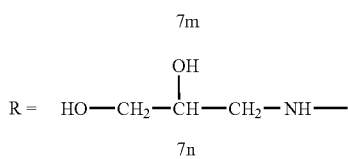
7n

R = 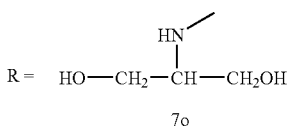
7o

R = 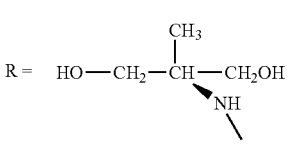
7p

R = 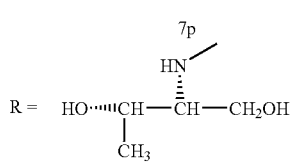
7q

R = 
7r

R = 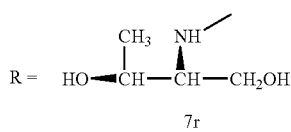
7s

R = 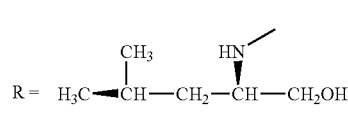
7t

R = 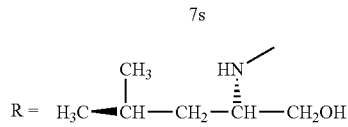
7u

R = 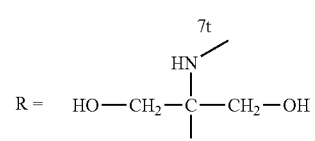
7v

The conjugations of rapamycin with amino alcohols or peptides comprising an amino alcohol at the "C" terminal of the peptide provides increased hydrophilic character to the compound by virtue of the presence of the free hydroxyl group.

Other rapamycin conjugates (7w, 7x, 7y) exhibiting increase hydrophilicity are shown in sheet 2 below.

Sheet 2

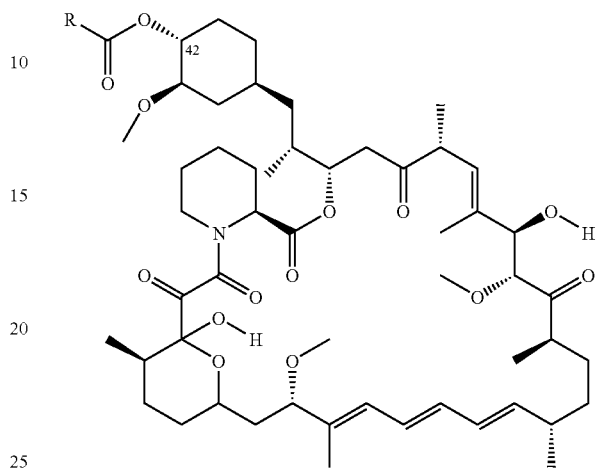

7

R = 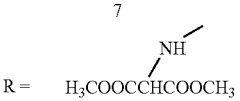
7w

R = 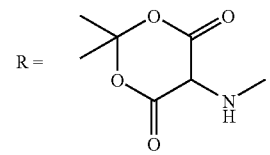
7x

R = 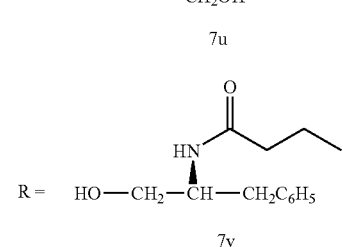
7y

The resulting compounds were screened on a panel of nine human tumor cell lines as listed in Table 1.

Quantification of cell proliferation and cell viability was determined by measuring the amount of radioactive [$^3$H-methyl]-thymidine incorporated into DNA. The detailed experimental procedure is further described below.

TABLE 1

Inhibition of $H^3$ Thymidine uptake ($IC_{50}$ in nM)

| Compound | A431 | Lncap | LS174T | MCF-7 | OVCAR-3 | SKMEL-2 | SK-N-SH | SKOV-3 | D341 |
|---|---|---|---|---|---|---|---|---|---|
| Adriamycin | 50.42 | 2.544 | 4.036 | 3.11 | 4.773 | 1.93 | 0.8959 | 129.7 | 7.016 |
| 5 | 341.2 | 30.33 | 979.6 | 0.4077 | 44.55 | 1.122 | 1.329 | 0.3916 | 1.561 |
| 7a | 607.9 | 153.6 | 625.6 | 29.61 | 415.9 | 78.06 | 86.93 | 80.02 | 138.2 |
| 7b | 1838 | 308.6 | 1485 | 53.32 | 423.6 | 325.5 | 143.6 | 135.5 | 182.5 |
| 7c | 286.4 | 211.8 | 1698 | 32.3 | 260.1 | 87.37 | 110.8 | 72.12 | 113.6 |
| 7d | 12748 | 197.9 | NE | 52.18 | 343.1 | 358.1 | 137.2 | 94.35 | 139.6 |
| 7e | 489.8 | 190.6 | 145.6 | 66.89 | 503.1 | 155.3 | 90.01 | 76.58 | 82.75 |
| 7f | NE | NE | NE | NE | NE | NE | NE | NE | NE |
| 7g | NE | NE | 3684 | 2437 | NE | 945.9 | NE | 595.1 | 936.7 |
| 7h | 2372 | 374.1 | 777 | 85.45 | 374.9 | 415.6 | 222.6 | 154.7 | 405.3 |
| 7i | 28361 | NE | NE | 1726 | 1667 | NE | NE | 13150 | 7717 |
| 7j | 505.7 | 166.3 | NE | 15.31 | 263.9 | 156.6 | 80.04 | 55.86 | 106.4 |
| 7k | 550.4 | 145.8 | 1380 | 15.94 | 295.9 | 109.2 | 71.32 | 66.03 | 259.4 |
| 7l | 216.8 | 64.62 | 23500 | 6.353 | 112.9 | 29.07 | 15.63 | 17.15 | 27.6 |
| 7m | 625.8 | 135.9 | 664 | 31.31 | 488.3 | 147.4 | 56.69 | 69.12 | 86.75 |
| 7n | 313.5 | 42.74 | 55081 | 2.5333 | 71.86 | 11.72 | 7.271 | 7.96 | 14.71 |
| 7o | 149.5 | 39.64 | 1027 | 2.579 | 80.73 | 48.34 | 5.837 | 27.44 | 36.16 |
| 7p | 254.3 | 7.119 | 2308 | 1.173 | 79.33 | 17.66 | 7.187 | 8.797 | 10.16 |
| 7q | 312.8 | 17.37 | 1631 | 1.291 | 56.47 | 9.154 | 5.253 | 6.346 | 25.21 |
| 7r | 190.8 | 21.76 | 1406 | 1.86 | 47.23 | 8.318 | 4.839 | 6.443 | 5.503 |
| 7s | 625 | 189 | NE | 15.59 | 355.4 | 153.9 | 97.29 | 93.64 | 103 |
| 7t | 277.9 | 202.4 | 23978 | 53.26 | 366.7 | 73.15 | 99.33 | 64.12 | 61.17 |
| 7u | 282.3 | 13.98 | 1594 | 1.539 | 56.62 | 6.152 | 6.402 | 8.078 | 20.83 |
| 7v | 1032 | 48.34 | NE | 5.522 | 95.46 | 81.01 | 18.78 | 10.36 | 15 |
| 7w | NE | 83.46 | 859.3 | 103.29 | NE | 378.4 | 164.11 | 26.51 | NE |
| 7x | NE | 3.32 | 432.8 | 7.091 | NE | 112.9 | 11.3 | 3.395 | NE |
| 7y | NE | 573.7 | 513.6 | 170 | NE | NE | 175.1 | 313.2 | NE |

As can be seen the compounds can be at least as efficient as rapamycin or in some instances the compounds are more efficient than rapamycin. The in vitro efficacy of rapamycin and rapamycin derivatives has been extensively correlated with the in vivo efficacy demonstrating that in vitro cell proliferation assays are highly predictive of in vivo efficacy (see for example Boffa et al. Clin Cancer Res. 2004, 1 (10): 293-300; Brown et al. PNAS 2003, 100 (25):15113-15118; Dudkin et al. Clin Cancer Res. 2001, 7 (6):1758-1764).

Without wishing to be bound by theory, the conjugation of peptides and/or amino acids or amino alcohols to rapamycin may provide a "bullet" capable of inactivating the functions of two or more proteins, such as $p27^{Kip1}$ and $p21^{Waf1/Cip1}$. This capacity to dual functional inactivation can be advantageous in cases where one of the target becomes resistant such as by mutation for example.

Thus the peptide and amino acid derivatives of rapamycin of the present invention are useful for the treatment of conditions in which the control or inhibition of the cell cycle is desirable. Such conditions may comprise but are not limited to: cancer (including solid tumors and leukemia/lymphoma), hyperplasia, psoriasis, fungal infections and the like. It will be appreciated that administration of the compounds of the present invention may be prophylactic to patients susceptible to the above mentioned conditions.

It will also be appreciated that the compounds of the present invention may also be used to treat or prevent hyperproliferative vascular disorders such as restenosis. In particular, the compounds may be applied to, or associated with, surgical stents to prevent restenosis at the site of the stent application in blood vessels. The compounds may for example be incorporated in drug-eluting stents or may be incorporated in a polymer coating applied to the stent. It will be appreciated that the compounds may also be administered to patients already having stents or about to receive such stents. Examples of methods for stent mediated delivery and/or stent coating are described in U.S. Pat. Nos. 6,808,536 and 6,585,764 which are herein incorporated by reference.

When used for restenosis, it is preferred that the compounds of this invention are used to treat restenosis that occurs following an angioplasty procedure.

The compounds are preferably administered as part of a pharmaceutical composition which may also comprise a pharmaceutically acceptable carrier as would be obvious to one skilled in the art.

Preferred routes for the administration of the compounds of the present invention are intravenous, intramuscular, subcutaneous, intraperitoneous, intraarterial, transdermal and oral. Transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal) It will be appreciated that other methods of administration, as would be known to one skilled in the art, may be used such as, for example, local administration at the site of a tumor using a catheter.

Catheter may be used to guide a carrier containing a compound or formulation of the present invention to be released by the carrier at a desired location. The catheter can be inserted in a lumen of a blood vessel or of the digestive tract for implanting the carrier. Such catheters are well known in the art.

Solutions or suspensions of these active compounds as a free base or pharmacologically acceptable salt can be prepared in water suitably mixed with a surfactant. Dispersions can also be prepared in glycerol, liquid polyethylene glycols and mixtures thereof in oils. Under ordinary conditions of storage and use, these preparation contain a preservative to prevent the growth of microorganisms.

The carrier for the injectable form of the compounds of the present invention can be a solvent or dispersion medium containing, for example, water, ethanol, polyol (e.g., glycerol, propylene glycol and liquid polyethylene glycol), suitable mixtures thereof, and vegetable oils.

It will be appreciated that the effective dosage of a rapamycin derivatives of the present invention may vary depending upon the particular compound utilized, the mode of administration, the condition, and severity thereof, of the condition being treated, as well as the various physical factors related to the individual being treated. Satisfactory results may be obtained when the rapamycin derivatives are administered in a daily dosage of about 0.1 μg/kg-100 mg/kg, preferably between 0.001-25 mg/kg, and more preferably between 0.01-5 mg/kg. The effective daily dosages are expected to vary with route of administration.

Oral formulations comprising the compound or composition of the present invention may be contained in conventional oral delivery means including capsules, tablets, and oral liquids and suspensions. The capsules may contain the compound of the present invention with an inert filler or diluent as are well known in the art. Oral formulations herein may utilize delay or time release formulations to tailor the pharmacokinetics of the active compound(s) to specific needs.

It is also possible to administer the compounds or composition of the invention directly to the airways in the form of an aerosol.

In another embodiment the compounds may be useful as immunosuppressants and can therefore be useful in treating diseases related to undesired immune responses. Non-limiting example includes preventing graft rejections (host vs graft disease, graft vs host disease), diseases of inflammation and autoimmune diseases such as arthritis.

Patients that are in need of the compounds and composition of the present invention may be identified or diagnosed by a person skilled in the art. For example, cancer diagnosis methods and apparatuses are routinely used and may include blood tests, X-ray radiography and the like.

Screening Procedure

1. Cell culture: For each cell line, culture was carried according to the ATCC Product Information Sheet provided. Cell lines were always freshly thawed prior to each experiment. For all experiments exponentially growing cells were harvested and centrifuged at 1100 rpm, the spent medium was aspirated and cell pellets were resuspended in fresh complete medium. Viable cells were enumerated by trypan blue exclusion using a hemacytometer.

2. Cells were then seeded in 96 well tissue culture plates in a total volume of 100 μL/well. A preliminary experiment should be performed to determine the most appropriate cell density for each individual cell line. Cells were allowed to attach and acclimate overnight.

3. Addition of test compounds: Each test compound was dissolved in DMSO at a final concentration of 2 mM. Each stock compound was then diluted in complete medium (1:100) to obtain a 20 μM working solution. The working solution was used for further serial dilutions to obtain concentrations of 200 nM, 20 nM, 2 nM, 0.2 nM and 0.02 nM. 100 μL of each dilution was added to the 100 μL cell cultures (3 replicates),. to give final test concentrations of 100 nM, 10 nM, 1 nM, 0.1 nM and 0.01 nM. Using this system of dilutions, the maximum concentration of DMSO to which the cells were exposed was 0.01% v/v. Therefore, 0.01% DMSO was added to control cells to which no test compounds was added. On each plate two positive controls were included: Adriamycin Hydrochloride and Rapamycin. For each positive control 3 concentrations were chosen in a range that achieved an $LC_{50}$, this range is cell line specific and must be predetermined in a pilot experiment. Plates were incubated for 96 hours prior to harvesting. [$^3$H-methyl]-thymidine incorporation: After 80 hours incubation, 10 μL (0.5 μCi) of [$^3$H-methyl]-thymidine diluted in 1× HBSS was added and plates were incubated overnight.

Growth medium was removed from each well and 100 uL of Trypsin-EDTA was added. The plate was incubated at 37° C. until cells were trypsinized (check under microscope). The detached cells were harvested using a semiautomatic cell harvester. Filters were dried prior to addition to scintillation vials. two mL of scintillation fluid was automatically dispensed into each vial and counting was effected on program 1 ($^3$H, 1 min, DPM).

The average and standard error from the DPM counts of replicate samples were calculated. The $IC_{50}$ values of these screening results are listed in Table 1.

EXAMPLE 1

Synthesis of Fmoc-NH-L-Ile-D-Phe-CH$_2$OH (1a)

(R)(+)-2-amino-3-phenyl-1-propanol (427 mg, 2.83 mmol) dissolved in dry DMF (20 mL), stirred under nitrogen, to this stirred mixture at 25° C. DCC (699 mg, 3.39 mmol), HOBt (457 mg, 3.38 mmol) was added with constant stirring. After 10 minutes of stirring N-(9-fluorenylmethoxycarbonyl)-L-isoleucine (1.0 g, 2.83 mmol) was added to the above mixture and then stirred at 25° C. for 14 h. After 14 h white colored crystals precipitated out (DCU), which was filtered. The filterate was checked on TLC (2% MeOH: CH$_2$Cl$_2$) which showed formation of a new compound at higher R$_f$ (0.6), LC/MS also showed molecular ion peak corresponding to the dipeptide 1a with other impurities peaks. The crude product was chromatographed on silica gel (Silica gel 60, 63-200μ) column and eluted with 2% MeOH: CH$_2$Cl$_2$ to give 650 mg of the dipeptide Fmoc-NH-L-Ile-D-Phe-CH$_2$OH (1a) as a white solid. Checked on LC/MS which showed M$^+$+1 (487.4) and M$^+$+Na (509.2).

EXAMPLE 2

Synthesis of Fmoc-NH-L-Ile-S-Phe-CH$_2$OH (1b)

S) (+)-2-amino-3-phenyl-1-propanol (1.3 g mg, 8.59 mmol) dissolved in dry DMF (100 mL), stirred under nitrogen, to this stirred mixture at. 25° C. DCC (1.94 g, 10.9 mmol), HOBt (1.27 g, 10.9 mmol) was added with constant stirring. After 10 minutes of stirring N-(9-fluorenylmethoxycarbonyl)-L-isoleucine (3.0 g, 2.83 mmol) was added to the above mixture and then, stirred at 25° C. for 14 h. After 14 h white colored crystals precipitated out (DCU), which was filtered. The filterate was checked on TLC (2% MeOH: CH$_2$Cl$_2$) which showed formation of a new compound at higher R$_f$(0.6), LC/MS also showed molecular ion peak corresponding to the dipeptide 1b with other impurities peaks. The crude product was chromatographed on silica gel (Silica gel 60, 63-200lμ) column and eluted with 2% MeOH: CH$_2$Cl$_2$ to give 2.8 g of the dipeptide Fmoc-NH-L-Ile-S-Phe-CH$_2$OH (1b) as a white solid. Checked on LC/MS which showed M$^+$+1 (487.2) and M$^+$+Na (509.2).

EXAMPLE 3

Synthesis of Fmoc-NH-L-Leu-L-Ile-D-Phe-CH$_2$OH (2a)

Dipeptide Fmoc-NH-L-Ile-D-Phe-CH$_2$OH (1a) (520 mg, 1.06 mmol) was taken in 20% piperidine in DMF (2 mL) and stirred for 15 minutes at 25° C., TLC examination showed complete removal of the Fmoc protecting group (NH$_2$-L-Ile-D-Phe-CH$_2$OH), further confirmed by LC/MS examination, which showed M$^+$−1 (263.3) peak. The reaction mixture was concentrated in vacuo, excess of the piperidine was removed by co-evaporating with toluene (2×10 mL), the free amino dipeptide was further dried over high vacumn for 30 minutes, and then redissolved in dry DMF (2 mL) and added to the mixture of N-(9-fluorenylmethoxycarbonyl)-L-leucine (38.1 mg, 1.06 mmol), DCC (262.0 mg, 1.27 mmol) and HOBt (171.4 mg, 1.27 mmol) in dry DMF (20 mL) at 25° C. The stirring was further continued for 14 h at 25° C. After 14 h white colored crystals precipitated out (DCU), which was filtered. The filterate was checked on TLC (3% MeOH: CH$_2$Cl$_2$) which showed formation of a new compound at higher R$_f$(0.5), LC/MS also showed molecular ion peak corresponding to the tripeptide 2a with other impurities peaks. The crude product was chromatographed on silica gel (Silica gel 60, 63-200µ) column and eluted with 3% MeOH: CH$_2$Cl$_2$ to give 310 mg of the tripeptide Fmoc-NH-L-Leu-L-Ile-D-Phe-CH$_2$OH (2a) as a white solid. Checked on LC/MS which showed M$^+$+1 (600.3) and M$^+$+Na (622.3).

EXAMPLE 4

Synthesis of Fmoc-NH-D-Leu-L-Ile-S-Phe-CH$_2$OH (2b)

Dipeptide Fmoc-NH-L-Ile-S-Phe-CH$_2$OH (1b) (2.0 g, 4.11 mmol) was taken in 20% piperidine in DMF (20 mL) and stirred for 15 minutes at 25° C., TLC examination showed complete removal of the Fmoc protecting group (NH$_2$-L-Ile-S-Phe-CH$_2$OH), further confirmed by LC/MS examination, which showed M$^+$−1 (263.3) peak. The reaction mixture was concentrated in vacuo, excess of the piperidine was removed by co-evaporating with toluene (2×20 mL), the free amino dipeptide was further dried over high vacumn for 30 minutes, and then redissolved in dry DMF (5 mL) and added to the mixture of N-(9-fluorenylmethoxycarbonyl)-D-leucine (1.59 g, 4.52 mmol), DCC (931 mg, 4.52 mmol) and HOBt (610.0 mg, 4.52 mmol) in dry DMF (150 mL) at 25° C. The stirring was further continued for 14 h at 25° C. After 14 h white colored crystals precipitated out (DCU), which was filtered. The filterate was checked on TLC (5% MeOH: CH$_2$Cl$_2$) which showed formation of a new compound at higher R$_f$ (0.5), LC/MS also showed molecular ion peak corresponding to the tripeptide 2b with other impurities peaks. The crude product was chromatographed on silica gel (Silica gel 60, 63-200µ) column and eluted with 4% MeOH: CH$_2$Cl$_2$ to give 450 mg of the tripeptide Fmoc-NH-D-Leu-L-Ile-S-Phe-CH$_2$OH (2b) as a white solid. Checked on LC/MS which showed M$^+$+1 (600.3) and M$^+$+Na (622.3).

EXAMPLE 5

Synthesis of Fmoc-NH-L-Ala-L-Leu-L-Ile-D-Phe-CH$_2$OH (3a)

Tripeptide Fmoc-NH-L-Leu-L-Ile-D-Phe-CH$_2$OH (2a) (75 mg, 0.125 mmol) was taken in 20% piperidine in DMF (0.5 mL) and stirred for 15 minutes at 25° C., TLC examination showed complete removal of the Fmoc protecting group (NH$_2$-L-Leu-L-Ile-D-Phe-CH$_2$OH), further confirmed by LC/MS examination, which showed M$^+$−1 (376.1) peak. The reaction mixture was concentrated in vacuo, excess of the piperidine was removed by co-evaporating with toluene (2×2 mL), the free amino tripeptide was further dried over high vacumn for 30 minutes, and then redissolved in dry DMF (0.5 mL) and added to the mixture of N-(9-fluorenylmethoxycarbonyl)-L-alanine (42.0 mg, 0.137 mmol), DCC (28.0 mg, 0.137 mmol) and HOBt (18.4 mg, 0.137 mmol) in dry DMF (2.5 mL) at 25° C. The stirring was further continued for 14 h at 25° C. After 14 h white colored crystals precipitated out (DCU), which was filtered. The filterate was checked on TLC (10% MeOH: CH$_2$Cl$_2$) which showed formation of a new compound at higher R$_f$(0.45), LC/MS also showed molecular ion peak corresponding to the tetrapeptide 3a with other impurities peaks. The crude product was chromatographed on silica gel (Silica gel 60, 63-200µ) column and eluted with 8% MeOH: CH$_2$Cl$_2$ to give 70 mg of the tetrapeptide Fmoc-NH-L-Ala-L-Leu-L-Ile-D-Phe-CH$_2$OH (3a) as a white solid. Checked on LC/MS which showed M$^+$+1 (671.3) and M$^+$+Na (693.3).

EXAMPLE 6

Synthesis of Fmoc-NH-D-Ala-D-Leu-L-Ile-S-Phe-CH$_2$OH (3b)

Tripeptide Fmoc-NH-D-Leu-D-Ile-S-Phe-CH$_2$OH (2b) (330 mg, 0.550 mmol) was taken in 20% piperidine in DMF (1.5 mL) and stirred for 15 minutes at 25° C., TLC examination showed complete removal of the Fmoc protecting group (NH$_2$-D-Leu-D-Ile-S-Phe-CH$_2$OH), further confirmed by LC/MS examination, which showed M−1 (376.1) peak. The reaction mixture was concentrated in vacuo, excess of the piperidine was removed by co-evaporating with toluene (2×5 mL), the free amino tripeptide was further dried over high vacumn for 30 minutes, and then redissolved in dry DMF (1.0 mL) and added to the mixture of N-(9-fluorenylmethdxycarbonyl)-D-alanine (188.4 mg, 0.606 mmol), DCC (124.0 mg, 0.606 mmol) and HOBt (81 mg, 0.606 mmol) in dry DMF (2.5 mL) at 25° C. The stirring was further continued for 14 h at 25° C. After 14 h white colored crystals precipitated out (DCU), which was filtered. The filterate was checked on TLC (10% MeOH: CH$_2$Cl$_2$) which showed formation of a new compound at higher R$_f$(0.40), LC/MS also showed molecular ion peak corresponding to the tetrapeptide 3b with other impurities peaks. The crude product was chromatographed on silica gel (Silica gel 60, 63-200µ) column and eluted with 7% MeOH: CH$_2$Cl$_2$ to give 40 mg of the tetrapeptide Fmoc-NH-D-Ala-D-Leu-D-Ile-S-Phe-CH$_2$OH (3b) as a white solid. Checked on LC/MS which showed M$^+$+1 (671.4) and M$^+$+Na (693.4).

EXAMPLE 7

Synthesis of N-α-Fmoc-N-Im(trityl)-D-His-L-Ala-L-Leu-L-Ile-D-Phe-CH$_2$OH (4a)

Tetrapeptide Fmoc-NH-L-Ala-L-Leu-L-Ile-D-Phe-CH$_2$OH (3a) (300 mg, 0.447 mmol) was taken in 20% piperidine in DMF (2.5 mL) and stirred for 15 minutes at 25° C., TLC examination showed complete removal of the Fmoc protecting group (NH$_2$-L-Ala-L-Leu-L-Ile-D-Phe-CH$_2$OH), further confirmed by LC/MS examination, which showed M$^+$+1 (450.3) peak. The reaction mixture was concentrated in vacuo, excess of the piperidine was removed by co-evaporating with toluene (2×5 mL), the free amino tetrapeptide was further dried over high vacumn for 30 minutes, and then redissolved in dry DMF (1.5 mL) and added to the mixture of N-α-(9-fluorenylmethoxycarbonyl)-N-Im(trityl)-D-histidine (304.8 mg, 0.492 mmol), DCC (101.3 mg, 0.492 mmol) and HOBt (66.4 mg, 0.492 mmol) in dry DMF (2.5 mL) at 25° C. The stirring was further continued for 14 h at 25° C. After 14 h white colored crystals precipitated out (DCU), which was filtered. The filterate was checked on TLC (15% MeOH: CH$_2$Cl$_2$) which showed formation of a new compound at higher R$_f$ (0.55), LC/MS also showed molecular ion peak corresponding to the pentapeptide 4a with other impurities peaks. The crude product was chromatographed on silica gel (Silica gel 60, 63-200µ) column and eluted with 10% MeOH: CH$_2$Cl$_2$ to give 376 mg of the pentapeptide N-α-Fmoc-N-Im (trityl)-D-His-L-Ala-L-Leu-L-Ile-D-Phe-CH$_2$OH (4a) as white solid. Checked on LC/MS which showed M$^+$+1 (1050.6).

EXAMPLE 8

Synthesis of N-α-Fmoc-N-Im(trityl)-L-His-L-Ala-L-Leu-L-Ile-D-Phe-CH$_2$OH (4b)

Tetrapeptide Fmoc-NH-L-Ala-L-Leu-L-Ile-D-Phe-CH$_2$OH (3a) (300 mg, 0.447 mmol) was taken in 20% piperidine in DMF (2.5 mL) and stirred for 15 minutes at 25° C., TLC examination showed complete removal of the Fmoc protecting group (NH$_2$-L-Ala-L-Leu-L-Ile-D-Phe-CH$_2$OH), further confirmed by LC/MS examination, which showed M$^+$+1 (450.3) peak. The reaction mixture was concentrated in vacuo, excess of the piperidine was removed by co-evaporating with toluene (2×5 mL), the free amino tetrapeptide was further dried over high vacumn for 30 minutes, and then redissolved in dry DMF (1.5 mL) and added to the mixture of N-α-(9-fluorenylmethoxycarbonyl)-N-Im(trityl)-L-histidine (304.8 mg, 0.492 mmol), DCC (101.3 mg, 0.492 mmol) and HOBt (66.4 mg, 0.492 mmol) in dry DMF (2.5 mL) at 25° C. The stirring was further continued for 14 h at 25° C. After 14 h white colored crystals precipitated out (DCU), which was filtered. The filterate was checked on TLC (15% MeOH: CH$_2$Cl$_2$) which showed formation of a new compound at higher R$_f$ (0.55), LC/MS also showed molecular ion peak corresponding to the pentapeptide 4b with other impurities peaks. The crude product was chromatographed on silica gel (Silica gel 60, 63-200µ) column and eluted with 10% MeOH: CH$_2$Cl$_2$ to give 376 mg of the pentapeptide N-α-Fmoc-N-Im (trityl)-L-His-L-Ala-L-Leu-L-Ile-D-Phe-CH$_2$OH (4b) as white solid. Checked on LC/MS which showed M$^+$+1 (1050.6).

EXAMPLE 9

42-O-(4-Nitrophenoxycarbonyl) rapamycin (6)

To a solution of 5.00 g (5.47 mmol) of rapamycin (5) in 40 ml of dichloromethane cooled at −78° C. with dry ice and acetone bath was added 650 µl of dry pyridine and 1.65 g of p-nitrophenyl chloroformate dissolved in 10 ml of dichloromethane. The reaction mixture was allowed to warm to ambient temperature and stirred for two hours under nitrogen. After two hours 325 µl of dry pyridine and 555 mg of the p-nitrophenyl chloroformate was added to the above reaction mixture. The reaction mixture was stirred under nitrogen for 18 h. The progress of the reaction was monitored by mass spectrum. After 18 h the reaction mixture was concentrated in vacuum and partitioned between ether and water. The organic phase was washed with 0.1N HCl (3×400 ml) than with saturated brine solution (2×100 ml), dried over sodium sulphate, filtered and concentrated in vacuum to give the pale yellow solid, which was purified on silica gel (Silica gel 60, 63-200µ). Elution with 40% and then 50% ethyl acetate: Hexane gave 4.7 g of the title compound (6) as yellow solid.

$^1$H NMR (CDCl$_3$): 67 8.27 and 7.39 (aromatic-H, 4H), 4.63 (42 C, 1H): Mass spectra: Positive M+Na 1101.5 (100%): Negative M−1 1077.5 (100%).

EXAMPLE 10

Synthesis of Rapamycin-42-O-ester-(NH-L-Ile-D-Phe-CH$_2$OH) (7a)

Dipeptide Fmoc-NH-L-Ile-D-Phe-CH$_2$OH (1a) (67.0 mg, 0.138 mmol) was taken in 20% piperidine in DMF (0.5 mL) and stirred for 15 minutes at 25° C., TLC examination showed complete removal of the Fmoc protecting group (NH$_2$-L-Ile-D-Phe-CH$_2$OH), further confirmed by LC/MS examination, which showed M$^+$−1 (263.3) peak. The reaction mixture was concentrated in vacuo, excess of the piperidine was removed by co-evaporating with toluene (2×2.5 mL), the free amino dipeptide was further dried over high vacumn for 30 minutes, and then redissolved in dry DMF (2 mL) and added to the mixture of 42-O-(4-Nitrophenoxycarbonyl) rapamycin (6) (100 mg, 0.092 mmol) and pyridine (50 µL)in dry DMF (10 mL) at 25° C. The stirring was further continued for 14 h at 25° C. After 14 h reaction mixture was checked on TLC (pure ethyl acetate) which showed formation of a new compound at lower R$_f$ (0.5) then the starting material, LC/MS also showed molecular ion peak corresponding to the conjugated product 7a with other impurities peaks. The crude product was chromatographed on silica gel (Silica gel 60, 63-200µ) column and eluted with pure ethyl acetate to afford 50 mg (45% yield) of the conjugate Rapamycin-42-O-ester-(NH-L-Ile-D-Phe-CH$_2$OH) 7a as a light yellow colored solid. Checked on LC/MS which showed M−1 1202.7 (100%).

EXAMPLE 11

Synthesis of Rapamycin-42-O-ester-(NH-L-Ile-S-Phe-CH$_2$OH) (7b)

Dipeptide Fmoc-NH-L-Ile-S-Phe-CH$_2$OH (1b) (67.0 mg, 0.138 mmol) was taken in 20% piperidine in DMF (0.2 mL) and stirred for 15 minutes at 25° C., TLC examination showed complete removal of the Fmoc protecting group (NH$_2$-L-Ile-S-Phe-CH$_2$OH), further confirmed by LC/MS examination, which showed M$^+$−1 (263.3) peak. The reaction mixture was concentrated in vacuo, excess of the piperidine was removed by co-evaporating with toluene (2×2.5 mL), the free amino dipeptide was further dried over high vacumn for 30 minutes, and then redissolved in dry DMF (2 mL) and added to the mixture of 42-O-(4-Nitrophenoxycarbonyl) rapamycin (6) (100 mg, 0.092 mmol) and pyridine (50 µL)in dry DMF (10 mL) at 25° C. The stirring was further continued for 14 h at 25° C. After 14 h reaction mixture was checked on TLC (pure ethyl acetate) which showed formation of a new compound at lower R$_f$(0.4) then the starting material, LC/MS. also showed molecular ion peak corresponding to the conjugated product 7b with other impurities peaks. The crude product was chromatographed on silica gel (Silica gel 60, 63-200µ) column and eluted with pure ethyl acetate to afford 18.8 mg (20% yield) of the conjugate Rapamycin-42-O-ester-(NH-L-Ile-S-Phe-CH$_2$OH) 7b as a light yellow colored solid. Checked on LC/MS which showed M−1 1202.6 (100%).

EXAMPLE 12

Synthesis of Rapamycin-42-O-ester-(NH-L-Leu-L-Ile-D-Phe-CH$_2$OH) (7c)

Dipeptide Fmoc-NH-L-Leu-L-Ile-D-Phe-CH$_2$OH (2a) (60.6 mg, 0.101 mmol) was taken in 20% piperidine in DMF (0.3 mL) and stirred for 15 minutes at 25° C., TLC examination showed complete removal of the Fmoc protecting group (NH$_2$-L-Leu-L-Ile-D-Phe-CH$_2$OH), further confirmed by LC/MS examination, which showed M$^+$−1 (376.1) peak. The reaction mixture was concentrated in vacuo, excess of the piperidine was removed by co-evaporating with toluene (2×2.5 mL), the free amino tripeptide was further dried over high vacumn for 30 minutes, and then redissolved in dry DMF (2 mL) and added to the mixture of 42-O-(4-Nitrophenoxycarbonyl) rapamycin (6) (100 mg, 0.092 mmol) and pyridine (50 µL) in dry DMF (10 mL) at 25° C. The stirring was further continued for 14 h at 25° C. After 14 h reaction mixture was checked on TLC (pure ethyl acetate) which showed formation of a new compound at lower R$_f$ (0.5) then the starting material, LC/MS also showed molecular ion peak corresponding to the conjugated product 7c with other impurities peaks. The crude product was chromatographed on silica gel (Silica gel 60, 63-200µ) column and eluted with pure ethyl acetate to afford 45 mg (37% yield) of the conjugate Rapamycin-42-O-ester-(NH-L-Leu-L-Ile-D-Phe-CH$_2$OH) 7c as a white solid. Checked on LC/MS which showed M−1 1315.6 (100%).

EXAMPLE 13

Synthesis of Rapamycin-42-O-ester-(NH-D-Leu-L-Ile-S-Phe-CH$_2$OH) (7d)

Dipeptide Fmoc-NH-D-Leu-L-Ile-S-Phe-CH$_2$OH (2b) (60.6 mg, 0.101 mmol) was taken in 20% piperidine in DMF (1.0 mL) and stirred for 15 minutes at 25° C., TLC examination showed complete removal of the Fmoc protecting group (NH$_2$-D-Leu-L-Ile-S-Phe-CH$_2$OH), further confirmed by LC/MS examination, which showed M$^+$−1 (376.1) peak. The reaction mixture was concentrated in vacuo, excess of the piperidine was removed by co-evaporating with toluene (2×5.0 mL), the free amino tripeptide was further dried over high vacumn for 30 minutes, and then redissolved in dry DMF (2 mL) and added to the mixture of 42-O-(4-Nitrophenoxycarbonyl) rapamycin (6) (100 mg, 0.092 mmol) and pyridine (50 µL) in dry DMF (10 mL) at 25° C. The stirring was further continued for 14 h at 25° C. After 14 h reaction mixture was checked on TLC (pure ethyl acetate) which showed formation of a new compound at lower R$_f$ (0.45) then the starting material, LC/MS also showed molecular ion peak corresponding to the conjugated product 7d with other impurities peaks. The crude product was chromatographed on silica gel (Silica gel 60, 63-200µ) column and eluted with pure ethyl acetate to afford 44 mg (36% yield) of the conjugate Rapamycin-42-O-ester-(NH-D-Leu-L-Ile-S-Phe-CH$_2$OH) 7d as a white solid. Checked on LC/MS which showed M−1 1315.6 (100%).

EXAMPLE 14

Synthesis of Rapamycin-42-O-ester-(NH-L-Ala-L-Leu-L-Ile-D-Phe-CH$_2$OH) (7e)

Tetrapeptide Fmoc-NH-L-Ala-L-Leu-L-Ile-D-Phe-CH$_2$OH (3a) (60 mg, 0.089 mmol) was taken in 20% piperidine in DMF (1.5 mL) and stirred for 15 minutes at 25° C., TLC examination showed complete removal of the Fmoc protecting group (NH$_2$-L-Ala-L-Leu-L-Ile-D-Phe-CH$_2$OH), further confirmed by LC/MS examination, which showed M$^+$+1 (450.3) peak. The reaction mixture was concentrated in vacuo, excess of the piperidine was removed by co-evaporating with toluene (2×2.5 mL), the free amino tetrapeptide was further dried over high vacumn for 30 minutes, and then redissolved in dry DMF (1.5 mL) and added to the mixture of 42-O-(4-Nitrophenoxycarbonyl) rapamycin (6) (100 mg, 0.092 mmol) and pyridine (50 µL) in dry DMF (10 mL) at 25° C. The stirring was further continued for 14 h at 25° C. After 14 h reaction mixture was checked on TLC (5% MeOH: CH$_2$Cl$_2$) which showed formation of a new compound at lower R$_f$ (0.45) then the starting material, LC/MS also showed molecular ion peak corresponding to the conjugated product 7e with other impurities peaks. The crude product was purified on preparative TLC using 5% MeOH: CH$_2$Cl$_2$ as the developing solvent system to afford 9.8 mg (10% yield) of the conjugate Rapamycin-42-O-ester-(NH-L-Ala-L-Leu-L-Ile-D-Phe-CH$_2$OH) 7e as a white solid. Checked on LC/MS which showed M$^+$+Na 1410.8 (100%).

EXAMPLE 15

Synthesis of Rapamycin-42-O-ester-(NH-D-Ala-D-Leu-L-Ile-S-Phe-CH$_2$OH) (7f)

Tetrapeptide Fmoc-NH-D-Ala-D-Leu-L-Ile-S-Phe-CH$_2$OH (3b) (60 mg, 0.089 mmol.) was taken in 20% piperidine in DMF (1.5 mL) and stirred for 15 minutes at 25° C., TLC examination showed complete removal of the Fmoc protecting group (NH$_2$-D-Ala-D-Leu-L-Ile-S-Phe-CH$_2$OH), further confirmed by LC/MS examination, which showed M$^+$+1 (450.3) peak. The reaction mixture was concentrated in vacuo, excess of the piperidine was removed by co-evaporating with toluene (2×2.5 mL), the free amino tetrapeptide was further dried over high vacumn for 30 minutes, and then redissolved in dry DMF (1.5 mL) and added to the mixture of 42-O-(4-Nitrophenoxycarbonyl) rapamycin (6) (100 mg, 0.092 mmol) and pyridine (50 µL) in dry DMF (10 mL) at 25° C. The stirring was further continued for 14 h at 25° C. After 14 h reaction mixture was checked on TLC (5% MeOH: CH$_2$Cl$_2$) which showed formation of a new compound at lower R$_f$ (0.45) then the starting material, LC/MS also showed molecular ion peak corresponding to the conjugated product 7f with other impurities peaks. The crude product was purified on preparative TLC using 5% MeOH: CH$_2$Cl$_2$ as the developing solvent system to afford 12.3 mg (11% yield) of the conjugate Rapamycin-42-O-ester-(NH-D-Ala-D-Leu-L-Ile-S-Phe-CH$_2$OH) 7f as a white solid. Checked on LC/MS which showed M$^+$+Na 1410.8 (100%).

EXAMPLE 16

Synthesis of Rapamycin-42-O-ester-(NH-N-Im(Trityl)-D-His-L-Ala-L-Leu-L-Ile-D-Phe-CH$_2$OH (7 g)

Pentapeptide N-α-Fmoc-N-Im(trityl)D-His-L-Ala-L-Leu-L-Ile-D-Phe-CH$_2$OH (4) (150 mg, 0.142 mmol) was taken in 20% piperidine in DMF (2.5 mL) and stirred for 15 minutes at 25° C., TLC examination showed complete removal of the Fmoc protecting group (NH$_2$-N-Im(trityl)-D-His-L-Ala-L-Leu-L-Ile-D-Phe-CH$_2$OH), further confirmed by LC/MS examination, which showed M$^+$+1 (828) peak. The reaction mixture was concentrated in vacuo, excess of the piperidine was removed by co-evaporating with toluene (2×5 mL), the free amino pentapeptide was further dried over high vacumn for 30 minutes, and then redissolved in dry DMF (1.5 mL) and added to the mixture of 42-O-(4-Nitrophenoxycarbonyl) rapamycin (6) (158 mg, 0.147 mmol) and pyridine (50 µL) in dry DMF (10 mL) at 25° C. The stirring was further continued for 14 h at 25° C. After 14 h reaction mixture was checked on TLC (5%. MeOH: CH$_2$Cl$_2$) which showed formation of a new compound at lower R$_f$ (0.45) then the starting material, LC/MS also showed molecular ion peak corresponding to the conjugated product 7 g with other impurities peaks The crude product was chromatographed on silica gel (Silica gel 60, 63-200μ) column and eluted with pure 10% MeOH: $CH_2Cl_2$ to afford 41 mg (16% yield) of the conjugate Rapamycin-42-O-ester-(NH-N-Im(Trityl)-D-His-L-Ala-L-Leu-L-Ile-D-Phe-$CH_2OH$ (7 g) as a white solid. Checked on LC/MS which showed M−1 1765.6 (90%) and 1766.8 (100%).

EXAMPLE 17

Synthesis of Rapamycin-42-O-ester-(NH-N-Im(Trityl)-L-His-L-Ala-L-Leu-L-Ile-D-Phe-$CH_2OH$ (7 h)

Pentapeptide N-α-Fmoc-N-Im(trityl)-L-His-L-Ala-L-Leu-L-Ile-D-Phe-$CH_2OH$ (4b) (150 mg, 0.142 mmol) was taken in 20% piperidine in DMF (2.5 mL) and stirred for 15 minutes at 25° C., TLC examination showed complete removal of the Fmoc protecting group ($NH_2$-N-Im(trityl)-D-His-L-Ala-L-Leu-L-Ile-D-Phe-$CH_2OH$), further confirmed by LC/MS examination, which showed $M^+$+1 (828) peak. The reaction mixture was concentrated in vacuo, excess of the piperidine was removed by co-evaporating with toluene (2×5 mL), the free amino pentapeptide was further dried over high vacumn for 30 minutes, and then redissolved in dry DMF (1.5 mL) and added to the mixture of 42-O-(4-Nitrophenoxycarbonyl) rapamycin (6) (158 mg, 0.147 mmol) and pyridine (50 μL) in dry DMF (10 mL) at 25° C. The stirring was further continued for 14 h at 25° C. After 14 h reaction mixture was checked on TLC (5% MeOH: $CH_2Cl_2$) which showed formation of a new compound at lower $R_f$ (0.45) then the starting material, LC/MS also showed molecular ion peak corresponding to the conjugated product 7h with other impurities peaks The crude product was chromatographed on silica gel (Silica gel 60, 63-200μ) column and eluted with pure 10% MeOH: $CH_2Cl_2$ to afford 41 mg (16% yield) of the conjugate Rapamycin-42-O-ester-(NH-N-Im(Trityl)-L-His-L-Ala-L-Leu-L-Ile-D-Phe-$CH_2OH$ (7h) as a white solid. Checked on LC/MS which showed M−1 1765.6 (90%) and 1766.8 (100%).

EXAMPLE 18

Synthesis of $NH_2$-N-Im(Trityl)-L-His-L-Ala-L-Lys-L-Arg-L-Arg-L-Leu-L-Ile-D-Phe-$CH_2OH$ (7i)

Octapeptide (7i) was synthesized by the reported procedure (Atkinson, G. E et al. Bioorganic Med. Chem. Lett. 2002, 12, 2501-2505) using solid phase method by solid phase method on a peptide synthesizer., LCMS 1039.5379 (100%)

EXAMPLE 19

Synthesis of Rapamycin-42-O-ester-(S) (−)-2-amino-3-phenyl-1-propanol (7j)

The active ester 42-O-(4-Nitrophenoxycarbonyl) rapamycin (6) 250 mg (0.231 mmol) was dissolved in dry N,N-dimethylformamide (10 mL) and to it. 50 μL dry pyridine was added, the reaction mixture was stirred under nitrogen for five minutes at 25° C. To this stirred solution 38.5 mg (0.225 mmol) of (S) (−)-2-amino-3-phenyl-1-propanol dissolved in 1 ml of N,N-dimethylformamide was added over a period of 10 minutes with constant stirring. Stirring under nitrogen was continued for 18 h at 25° C. The progress of the reaction was monitored by TLC (ethyl acetate, $R_f$ 0.5) and mass spectrum. After 18 h of the stirring the reaction mixture was evaporated to dryness. The crude mixture was purified on silica gel (Silica gel 60, 63-200μ) column chromatography, by step gradient from 10 to 50% of ethyl acetate: hexane and then pure ethyl acetate to give Rapamycin-42-O-ester-(S) (−)-2-amino-3-phenyl-1-propanol (7j) as beige colored solid 150 mg (60% yield), LC/MS showed $M^+$+Na 1113.8 (100%) and M−1 1069.8 (100%).

EXAMPLE 20

Synthesis of Rapamycin-42-O-ester-(R) (+)-2-amino-3-phenyl-1-propanol (7 k)

The active ester 42-O-(4-Nitrophenoxycarbonyl) rapamycin (6) 125 mg (0.115 mmol) was dissolved in dry N,N-dimethylformamide (10 mL) and to it 50 μL dry pyridine was added, the reaction mixture was stirred under nitrogen for five minutes at 25° C. To this stirred solution 19.2 mg (0.127 mmol) of (R) (+)-2-amino-3-phenyl-1-propanol dissolved in 1 ml of N,N-dimethylformamide was added over a period of 10 minutes with constant stirring. Stirring under nitrogen was continued for 18 h at 25° C. The progress of the reaction was monitored by TLC (ethyl acetate, $R_f$ 0.6) and mass spectrum. After 18 h of the stirring the reaction mixture was evaporated to dryness. The crude mixture was purified on silica gel (Silica gel 60, 63-200μ) column chromatography, by step gradient from 10 to 50% of ethyl acetate: hexane and then pure ethyl acetate to give Rapamycin-42-O-ester-(R) (+)-2-amind-3-phenyl-1-propanol (7k) as beige colored solid 65 mg (51% yield), LC/MS showed M−1 1069.8 (100%).

EXAMPLE 21

Synthesis of Rapamycin-42-O-ester-(1S,2S)-(+)-2-amino-1-phenyl-1,3-propandiol (71)

The active ester 42-O-(4-Nitrophenoxycarbonyl) rapamycin (6) 150 mg (0.139 mmol) was dissolved in dry N,N-dimethylformamide (10 mL) and to it 50 μL dry pyridine was added, the reaction mixture was stirred under nitrogen for five minutes at 25° C. To this stirred solution 25.5 mg (0.139 mmol) of (1S,2S)-(+)-2-amino-1-phenyl-1,3-propandiol dissolved in 1 ml of N,N-dimethylformamide was added over a period of 10 minutes with constant stirring. Stirring under nitrogen was continued for 18 h at 25° C. The progress of the reaction was monitored by TLC (ethyl acetate, $R_f$ 0.4) and mass spectrum. After 18 h of the stirring the reaction mixture was evaporated to dryness. The crude mixture was purified on silica gel (Silica gel 60, 63-200μ) column chromatography, by step gradient from 10 to 50% of ethyl acetate: hexane and then pure ethyl acetate to give Rapamycin-42-O-ester-(1S, 2S)-(+)-2-amino-1-phenyl-1,3-propandiol (71) as white colored solid 62.3 mg (41% yield), LC/MS showed M−1 1105.7 (100%).

EXAMPLE 22

Synthesis of Rapamycin-42-O-ester-2-amino-3-methyl-1-pentanol (7m)

The active ester 42-O-(4-Nitrophenoxycarbonyl) rapamycin (6) 100 mg (0.092 mmol) was dissolved in dry N,N-dimethylformamide (6 mL) and to it 50 μL dry pyridine was added, the reaction mixture was stirred under nitrogen for five minutes at 25° C. To this stirred solution 11.8 mg (0.101 mmol) of 2-amino-3-methyl-1-pentanol dissolved in 1 ml of N,N-dimethylformamide was added over a period of 10 minutes with constant stirring. Stirring under nitrogen was continued for 18 h at 25° C. The progress of the reaction was monitored by TLC (ethyl acetate, $R_f$ 0.6) and mass spectrum. After 18 h of the stirring the reaction mixture was evaporated to dryness. The crude mixture was purified on silica gel (Silica gel 60, 63-200μ) column chromatography, by step gradient from 10 to 50% of ethyl acetate: hexane and then pure ethyl acetate to give Rapamycin-42-O-ester-2-amino-3-methyl-1-pentanol (7m) as white colored solid 50 mg (52% yield), LC/MS showed M−1 1055.7 (100%).

EXAMPLE 23

Synthesis of Rapamycin-42-O-ester-3-amino-1,2-propanediol (7n)

The active ester 42-O-(4-Nitrophenoxycarbonyl) rapamycin (6) 100 mg (0.092 mmol) was dissolved in dry N,N-dimethylformamide (5 mL) and to it 50 μL dry pyridine was added, the reaction mixture was stirred under nitrogen for five minutes at 25° C. To this stirred solution 9.29 mg (0.102 mmol) of 3-amino-1,2-propanediol dissolved in 1 ml of N,N-dimethylformamide was added over a period of 10 minutes with constant stirring. Stirring under nitrogen was continued for 18 h at 25° C. The progress of the reaction was monitored by TLC (10% MeOH: $CH_2Cl_2$, $R_f$ 0.4) and mass spectrum. After 18 h of the stirring the reaction mixture was evaporated to dryness. The crude mixture was purified on silica gel (Silica gel 60, 63-200μ) column chromatography, by step gradient from pure $CH_2Cl_2$ to 10% MeOH: $CH_2Cl_2$ to give Rapamycin-42-O-ester-3-amino-1,2-propanediol (7n) as white colored solid 30 mg (31% yield), LC/MS showed M−1 1029.6 (100%).

EXAMPLE 24

Synthesis of Rapamycin-42-O-ester-2-amino-1,3-propanediol (7o)

The active ester 42-O-(4-Nitrophenoxycarbonyl) rapamycin (6) 100 mg (0.092 mmol) was dissolved in dry N,N-dimethylformamide (5 mL) and to it 50 μL dry pyridine was added, the reaction mixture was stirred under nitrogen for five minutes at 25° C. To this stirred solution 9.29 mg (0.102 mmol) of 3-amino-1,3-propanediol dissolved in 1 ml of N,N-dimethylformamide was added over a period of 10 minutes with constant stirring. Stirring under nitrogen was continued for 18 h at 25° C. The progress of the reaction was monitored by TLC (10% MeOH: $CH_2Cl_2$, $R_f$ 0.4) and mass spectrum. After 18 h of the stirring the reaction mixture was evaporated to dryness. The crude mixture was purified on silica gel (Silica gel 60, 63-200μ) column chromatography, by step gradient from pure $CH_2Cl_2$ to 7% MeOH: $CH_2Cl_2$ to give Rapamycin-42-O-ester-3-amino-1,3-propanediol (7o) as white colored solid 50 mg (52% yield), LC/MS showed M−1 1029.5 (100%).

EXAMPLE 25

Synthesis of Rapamycin-42-O-ester-2-amino-2-methyl-1,3-propanediol (7p)

The active ester 42-O-(4-Nitrophenoxycarbonyl) rapamycin (6) 100 mg (0.092 mmol) was dissolved in dry N,N-dimethylformamide (5 mL) and to it 50 μL dry pyridine was added, the reaction mixture was stirred under nitrogen for five minutes at 25° C. To this stirred solution 9.7 mg (0.092 mmol) of 2-amino-2-methyl-1,3-propanediol dissolved in 1 ml of N,N-dimethylformamide was added over a period of 10 minutes with constant stirring. Stirring under nitrogen was continued for 18 h at 25° C. The progress of the reaction was monitored by TLC (10% MeOH: $CH_2Cl_2$, $R_f$ 0.6) and mass spectrum. After 18 h of the stirring the reaction mixture was evaporated to dryness. The crude mixture was purified on silica gel (Silica gel 60, 63-200μ) column chromatography, by step gradient from pure $CH_2Cl_2$ to 7% MeOH: $CH_2Cl_2$ to give Rapamycin-42-O-ester-2-amino-2-methyl-1,3-propanediol (7p) as white colored solid 31 mg (33% yield), LC/MS showed $M^+$+Na 1067.5 (100%).

EXAMPLE 26

Synthesis of Rapamycin-42-O-ester-(2S,3S)-2-amino-1,3-butanediol (7q)

The active ester 42-O-(4-Nitrophenoxycarbonyl) rapamycin (6) 100 mg (0.092 mmol) was dissolved in dry N,N-dimethylformamide (20 mL) and to it 50 μL dry pyridine was added, the reaction mixture was stirred under nitrogen for five minutes at 25° C. To this stirred solution 9.7 mg (0.092 mmol) of (2S,3S)-2-amino-1,3-butanediol dissolved in 1 ml of N,N-dimethylformamide was added over a period of 10 minutes with constant stirring. Stirring under nitrogen was continued for 18 h at 25° C. The progress of the reaction was monitored by TLC (10% MeOH: $CH_2Cl_2$, $R_f$ 0.6) and mass spectrum. After 18 h of the stirring the reaction mixture was evaporated to dryness. The crude mixture was purified on silica gel (Silica gel 60, 63-200μ) column chromatography, by step gradient from pure $CH_2Cl_2$ to 7% MeOH: $CH_2Cl_2$ to give Rapamycin-42-O-ester-(2S,3S)-2-amino-1,3-butanediol (7q) as beige colored solid 60 mg (62% yield), LC/MS showed $M^+$+Na 1067.7 (100%).

EXAMPLE 27

Synthesis of Rapamycin-42-O-ester-(2R,3R)-2-amino-1,3-butanediol (7r)

The active ester 42-O-(4-Nitrophenoxycarbonyl) rapamycin (6) 100 mg (0.092 mmol) was dissolved in dry N,N-dimethylformamide (15 mL) and to it 50 μL dry pyridine was added, the reaction mixture was stirred under nitrogen for five minutes at 25° C. To this stirred solution 9.7 mg (0.092 mmol) of (2R,3R)-2-amino-1,3-butanediol dissolved in 1 ml of N,N-dimethylformamide. was added over a period of 10 minutes with constant stirring. Stirring under nitrogen was continued for 18 h at 25° C. The progress of the reaction was monitored by TLC (10% MeOH: $CH_2Cl_2$, $R_f$ 0.5) and mass spectrum. After 18 h of the stirring the reaction mixture was evaporated to dryness. The crude mixture was purified on silica gel (Silica gel 60, 63-200μ) column chromatography, by step gradient from pure $CH_2Cl_2$ to 10% MeOH: $CH_2Cl_2$ to give Rapamycin-42-O-ester-(2R,3R)-2-amino-1,3-butanediol (7r) as white colored solid 65 mg (67% yield), LC/MS showed M−1 1043.6 (100%).

EXAMPLE 28

Synthesis of Rapamycin-42-O-ester-(R)-(−)-2-amino-4-methyl pentanol (7s)

The active ester 42-O-(4-Nitrophenoxycarbonyl) rapamycin (6) 100 mg (0.092 mmol) was dissolved in dry N,N-dimethylformamide. (5 mL) and to it 50 μL dry pyridine was added, the reaction mixture was stirred under nitrogen for five minutes at 25° C. To this stirred solution 10.8 mg (0.092 mmol) of (R)-(−)-2-amino-4-methyl pentanol dissolved in 1 ml of N,N-dimethylformamide was added over a period of 10 minutes with constant stirring. Stirring under nitrogen was continued for 18 h at 25° C. The progress of the reaction was monitored by TLC (10% MeOH: $CH_2Cl_2$, $R_f$ 0.5) and mass spectrum. After 18 h of the stirring the reaction mixture was evaporated to dryness. The crude mixture was purified on silica gel (Silica gel 60, 63-200μ) column chromatography, by step gradient from pure $CH_2Cl_2$ to 5% MeOH: $CH_2Cl_2$ to give Rapamycin-42-O-ester-(R)-(−)-2-amino-4-methyl pentanol (7s) as white colored solid 34 mg (35% yield), LC/MS showed $M^++Na$ 1079.7 (100%).

EXAMPLE 29

Synthesis of Rapamycin-42-O-ester-(S)-(+)-2-amino-4-methyl pentanol (7t)

The active ester 42-O-(4-Nitrophenoxycarbonyl) rapamycin (6) 100 mg (0.092 mmol) was dissolved in dry N,N-dimethylformamide (5 mL) and to it 50 μL dry pyridine was added, the reaction mixture was stirred under nitrogen for five minutes at 25° C. To this stirred solution 10.8 mg (0.092 mmol) of (S)-(+)-2-amino-4-methyl pentanol dissolved in 1 ml of N,N-dimethylformamide was added over a period of 10 minutes with constant stirring. Stirring under nitrogen was continued for 18 h at 25° C. The progress of the reaction was monitored by TLC (10% MeOH: $CH_2Cl_2$, $R_f$ 0.5) and mass spectrum. After 18 h of the stirring the reaction mixture was evaporated to dryness. The crude mixture was purified on silica gel (Silica gel 60, 63-200lμ) column chromatography, by step gradient from pure $CH_2Cl_2$ to 5% MeOH : $CH_2Cl_2$ to give Rapamycin-42-O-ester-(S)-(+)-2-amino-4-methyl pentanol (7t) as white colored solid 43 mg (40% yield), LC/MS showed $M^++Na$ 1079.7 (100%).

EXAMPLE 30

Synthesis of Rapamycin-42-O-ester-Tris(hydroxymethyl)amino methane (7u)

The active ester 42-O-(4-Nitrophenoxycarbonyl) rapamycin (6) 100 mg (0.092 mmol) was dissolved in dry N,N-dimethylformamide (5 mL) and to it 50 μL dry pyridine was added, the reaction mixture was stirred under nitrogen for five minutes at 25° C. To this stirred solution 12.35 mg (0.102 mmol) of tris(hydroxymethyl)amino methane dissolved in 1 ml of N,N-dimethylformamide was added over a period of 10 minutes with constant stirring. Stirring under nitrogen was continued for 18 h at 25° C. The progress of the reaction was monitored by TLC (10% MeOH: $CH_2Cl_2$, $R_f$ 0.5) and mass spectrum. After 18 h of the stirring the reaction mixture was evaporated to dryness. The crude mixture was purified on silica gel (Silica gel 60, 63-200μ) column chromatography, by step gradient from pure $CH_2Cl_2$ to 5% MeOH: $CH_2Cl_2$ to give Rapamycin-42-O-ester-tris(hydroxymethyl)amino methane (7u) as white colored solid 25 mg (30% yield), LC/MS showed $M^++Na$ 1083.6 (100%).

EXAMPLE 31

Synthesis of Rapamycin-42-O-(3-carboxy propanoyl) ester-(S) (−)-2-amino-3-phenyl-1-propanol (7v)

The active ester 42-O-(3-carboxy propanoyl) rapamycin (WO 94/24304) 75 mg (0.067 mmol) was dissolved in dry N,N-dimethylformamide (5 mL) and to it 40 μL dry pyridine was added, the reaction mixture was stirred under nitrogen for five minutes at 25° C. To this stirred solution 11.1 mg (0.074 mmol) of (S) (−)-2-amino-3-phenyl-1-propanol dissolved in 1 ml of N,N-dimethylformamide was added over a period of 10 minutes with constant stirring. Stirring under nitrogen was continued for 18 h at 25° C. The progress of the reaction was monitored by TLC (5% MeOH: $CH_2Cl_2$, $R_f$ 0.6) and mass spectrum. After 18 h of the stirring the reaction mixture was evaporated to dryness. The crude mixture was purified on silica gel (Silica gel 60, 63-200μ) column chromatography, by step gradient from pure $CH_2Cl_2$ to 4% MeOH: $CH_2Cl_2$ to give Rapamycin-42-O-(3-carboxy propanoyl) ester-(S) (−)-2-amino-3-phenyl-1-propanol (7v) as white colored solid 50 mg (50% yield), LC/MS showed $M^++Na$ 1145.4 (100%).

The embodiment(s) of the invention described above is(are) intended to be exemplary only. The scope of the invention is therefore intended to be limited solely by the scope of the appended claims.

We claim:
1. A compound of the formula

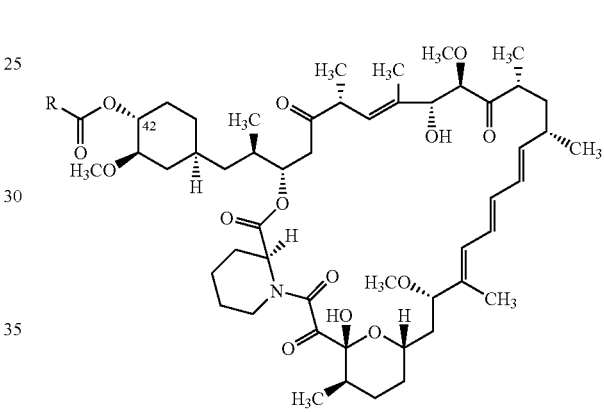

wherein,
R is $NH-(A)_n-CH_2OH$; or

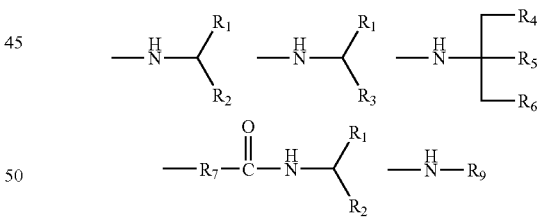

wherein R as defined above comprises an amino acid; an amino alcohol or a peptide;
A is D or L amino acid and n=1-10,
$R_1$ and $R_2$ are each independently, hydrogen, alkyl of 1-6 carbons atoms, hydroxyalkyl of 1-6 carbon atoms, or $CO_2R_8$,
$R_3$ is Ar, wherein Ar is aromatic or heteroaromatic;
$R_4$, $R_5$ and $R_6$ are each independently alkyl of 1-6 carbon atoms or hydroxyalkyl of 1-6 carbon atoms;
$R_7$ is alkyl of 1-10 carbon atoms;
$R_8$ is alkyl of 1-6 carbon atoms; and
$R_9$ is cycloalkoxyalkyl of 4-10 carbon atoms;
wherein R and said compound of formula I are linked through a carbamate ester linkage.

2. The compound of claim 1, wherein R is selected from: NH-L-Ile-D-Phe-CH₂OH, NH-L-Ile-S-Phe-CH₂OH, NH-L-Leu-L-Ile-D-Phe-CH₂OH, NH-D-Leu-L-Ile-S-Phe-CH₂OH, NH-L-Ala-L-Leu-L-Ile-D-Phe-CH₂OH, NH-D-Ala-D-Leu-L-Ile-S-Phe-CH₂OH, NH—N-Im(Trityl)D-His-L-Ala-L Leu-L Ile-D-Phe-CH₂OH, NH—N-Im(Trityl)D-His-L-Ala-L-Leu-L-Ile-D-Phe-CH₂OH, NH-L-His-L-Ala L Lys-L-Arg-L-Arg-L-Leu-L-Ile-D-Phe-CH₂OH,

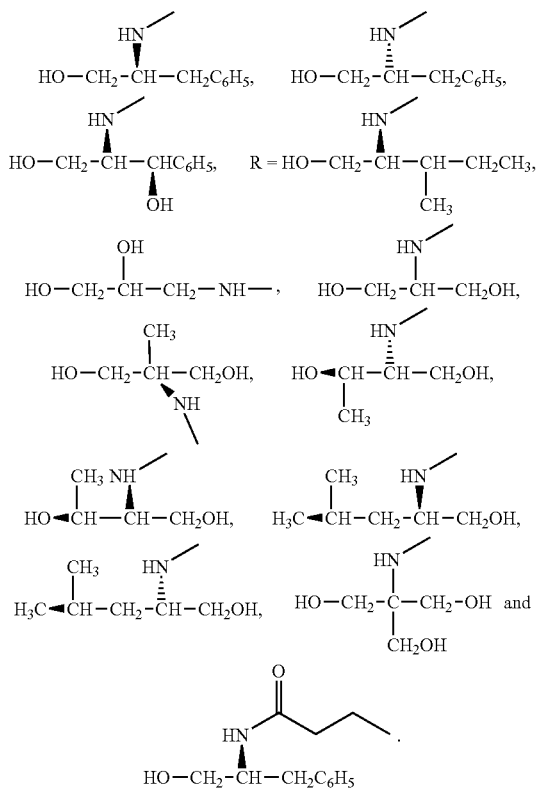

3. A pharmaceutical composition comprising the compound of claim 1 or 2, or a pharmaceutically acceptable salt thereof, and a pharmaceutically acceptable carrier.

4. A stent coated with the compound of claim 1 or 2.

5. The stent as claimed in claim 4, wherein said compound is comprised within a coating composition.

6. A stent coated with the composition of claim 3.

7. The stent as claimed in claim 6, wherein said compound is comprised within a coating composition.

8. A method for treating a cell proliferation disorder comprising administering the pharmaceutical composition as claimed in claim 3 to a patient in need thereof in an amount sufficient to reduce cell proliferation.

9. The method as claimed in claim 8 wherein said cell proliferation disorder is selected from cancer, hyperplasia, psoriasis and hyperproliferative vascular disease.

10. The method as claimed in claim 9 wherein said hyperproliferative vascular disease is restenosis.

11. The method as claimed in claim 9, wherein said composition is released from the carrier, said carrier being implanted at a desired location within said patient.

12. The method as claimed in claim 11 wherein said carrier is implanted using a vascular guiding means.

13. The method as claimed in claim 12 wherein said vascular guiding means is a cathether.

14. The method as claimed in claim 10, wherein said composition is released from the carrier, said carrier being implanted at a desired location within said patient.

15. The method as claimed in claim 11, wherein said carrier is implanted using a vascular guiding means.

16. The method as claimed in claim 12, wherein said vascular guiding means is a catheter.

17. A method for treating an immunological condition comprising administering the pharmaceutical composition as claimed in claim 3 to a patient in need thereof in an amount sufficient to suppress the immune system.

18. The method as claimed in claim 17 wherein said immunological disorder is selected from autoimmune disease and host-graft disease.

19. A process for the preparation of the compound of claim 1 or 2 comprising reacting 42-O-(4-Nitrophenoxycarbonyl) rapamycin and an amino acid or a peptide or an amino alcohol in the presence of a base.

20. The process as claimed in claim 19 wherein said base is pyridine.

* * * * *

UNITED STATES PATENT AND TRADEMARK OFFICE
CERTIFICATE OF CORRECTION

| | | |
|---|---|---|
| PATENT NO. | : 7,659,244 B2 | Page 1 of 1 |
| APPLICATION NO. | : 10/578105 | |
| DATED | : February 9, 2010 | |
| INVENTOR(S) | : Sharma et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 565 days.

Signed and Sealed this

Thirtieth Day of November, 2010

David J. Kappos
*Director of the United States Patent and Trademark Office*